US00PP08713P

United States Patent [19]

Lamb et al.

[11] Patent Number: Plant 8,713

[45] Date of Patent: May 3, 1994

[54] ANTHURIUM PLANT NAMED TAFFY

[75] Inventors: Ann E. Lamb; Robert D. Hartman, both of Lake Placid, Fla.

[73] Assignee: Twyford International, Inc., Santa Paula, Calif.

[21] Appl. No.: 64,695

[22] Filed: May 21, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named Taffy characterized by its abundant rose-pink flowers which are held above the foliage, upright compact habit, very abundant branches, and durable dark green shiny leaves.

1 Drawing Sheet

The present invention comprises a new and distinct cultivar of Anthurium, botanically known as *Anthurium hybrid,* and referred to by the cultivar name Taffy.

The new cultivar is a product of a planned breeding program carried out by the inventors Ann E. Lamb and Robert D. Hartman. The seedling is a result of a cross made between unidentified parents in Palmdale, Fla. The cultivar was discovered from the progeny of the stated cross by Ann E. Lamb. Asexual propagation by tissue culture in Palmdale increased the number of plants for evaluation, and has demonstrated the stability of the combination of characteristics of the new cultivar from generation to generation.

The following observations, measurements and values describe plants grown in Homestead, Fla. under shade house conditions which closely approximate those generally used in horticultural practice.

The following traits have been repeatedly observed to be characteristics which in combination distinguish Taffy from other Anthuriums of the same general type, for example, the well known cultivar Lady Jane.

1. The plant produces abundant rose-pink flowers which gradually fade to white.
2. The flowers are held above the foliage.
3. The leaves are dark green, have a shiny surface, and are durable.
4. The plant habit is compact and upright.
5. The plant is free branching.

All color references are made to The Royal Horticultural Society Colour Chart. Colors are as closely approximate as possible. Color and other phenotypic characteristics will vary somewhat depending on horticultural practices such as light level and fertilization rate, among others, without, however any variance in genotype.

The color photographic drawing comprises a top perspective view of the inflorescence and foliage of a plant of Taffy in a 25.5 cm pot. The photograph was taken approximately 69 weeks after planting a 20 week old liner of the new cultivar obtained by tissue culture and grown under appropriate growing conditions.

Origin: Seedling of unknown parentage.

Classification: *Anthurium hybrid,* cv, Taffy.

Propagation: Asexual production either by tissue culture or division.

Plant: When a 20 week liner is grown in a 25.5 cm pot for 69 weeks under appropriate growing conditions, Taffy will be at the mature size of approximately 35 cm. to 50 cm. in height and approximately 60 cm to 70 cm. in width.

Leaves:

*Form.*—The leaf blade is ovate with a cuspidate tip and an obtuse to cordate base. The margins are entire. The midrib tends to curve somewhat downward over the length of the leaf. The leaf blade tends to be slightly wavy over the width of the leaf.

*Size.*—Leaf blades of a mature sized plant will be approximately 19 cm to 21 cm in length and approximately 11 cm to 13 cm in width.

*Petiole.*—The petiole is approximately 19 cm to 20 cm in height from the base of the petiole to the base of the leaf blade on the primary shoot. Secondary shoots are somewhat smaller depending on the age of the shoot. The petiole is approximately 4.5 mm in diameter just below the geniculum, and straight.

*Petiole wings.*—Petiole wings are approximately 3 cm in length and approximately 5 mm in width at their midpoint. The tips of the petiole wings are cordate. There is approximately 13.5 cm to 14 cm between the top of the wing and the base of the geniculum.

*Geniculum.*—The geniculum is approximately 20 mm to 25 mm in length, approximately 5 mm in diameter, and is often curved. The color is 144A. There is no space between the top of the geniculum and the base of the leaf blade. The geniculum is prominent.

*Veins.*—Veins are sunken, with the leaf blade slightly convex between veins on the upper surface. The midrib protrudes from the upper surface of the leaf for approximately ⅔ the length of the leaf. Well defined primary veins on leaves radiate out from the juncture of the petiole and the leaf. Veins stand out prominently on the lower side. There are approximately 4–6 primary veins on the leaf.

*Lobes.*—The leaf has two rounded lobes which do not extend past the petiole. The distance from the petiole/leaf juncture to the highest point on the lobes is approximately 5.5 cm to 6.5 cm.

*Color.*—Upper surface: Closest to 139A but slightly lighter. Lower surface: 146B. Midrib, upper surface: 138A. Midrib, lower surface: 416D. Petiole: 146C, lower surface; Upper surface is 146C with a bronze cast when exposed to direct light. Petiole wing: 144B.

INFLORESCENCE

Immature: The spathe is tightly rolled around the spadix and extrudes from the petiole sheath. The spathe is fully open approximately when the pedicel is fully elongated, about 35 cm to 41 cm above the soil surface.

Mature:

*Spathe.*—Size: The flattened spathe is approximately 7.5 cm to 8.5 cm long and approximately 5 cm to 5.5 cm in width and 0.5 cm in depth. Color: Fully open: Upper surface: Pinker than 54C. Lower surface: Lighter than 56D. Faded: Upper surface: Whiter than 56D. Lower surface: 155A.

*Arrangement.*—The spathes stand up on straight wiry pedicels and open vertically above the leaves. Shape: The spathe is ovate with a cordate base and a cuspidate apice that is straight. It is slightly cupped when first open and is approximately 4 cm to 6.5 cm in height, 4 cm to 5.0 cm in width, and 0.5 cm in depth. The spathe flattens and reflexes slightly as it ages.

*Flowering time.*—After approximately 16–18 months from a 20 week old liner for an untreated plant as illustrated in photograph, and depending on season, approximately 10 to 12 blossoms will be present. Smaller blossoms may occur on less mature growth. First flowers (1 to 3) can be expected approximately 4–5 months after planting a 20 week old liner.

REPRODUCTIVE ORGANS

Spadix:

*Size.*—Approximately 4 cm to 4.5 cm in height and 8 mm to 9 mm in width.

*Color.*—When the spathe unrolls, the spadix is 54C (the spadix may be much darker, close to 186A, on very young plants), gradually changing to 145B with spots of pink, before senescing.

*Stamens.*—Anthers and filaments are not clearly visible.

*Pollen.*—White in color.

*Pistil.*—Lighter than 20C-D in color, protruding between the staminate flowers, firmly fixed to the main axil. The pistilate flowers extend approximately 0.5 mm beyond the staminate flowers.

Roots: White fleshy roots with fine laterals. Roots initiated above the soil have a light pink (48-B) cast.

We claim:

1. A new and distinct cultivar of Anthurium plant named Taffy, as illustrated and described.

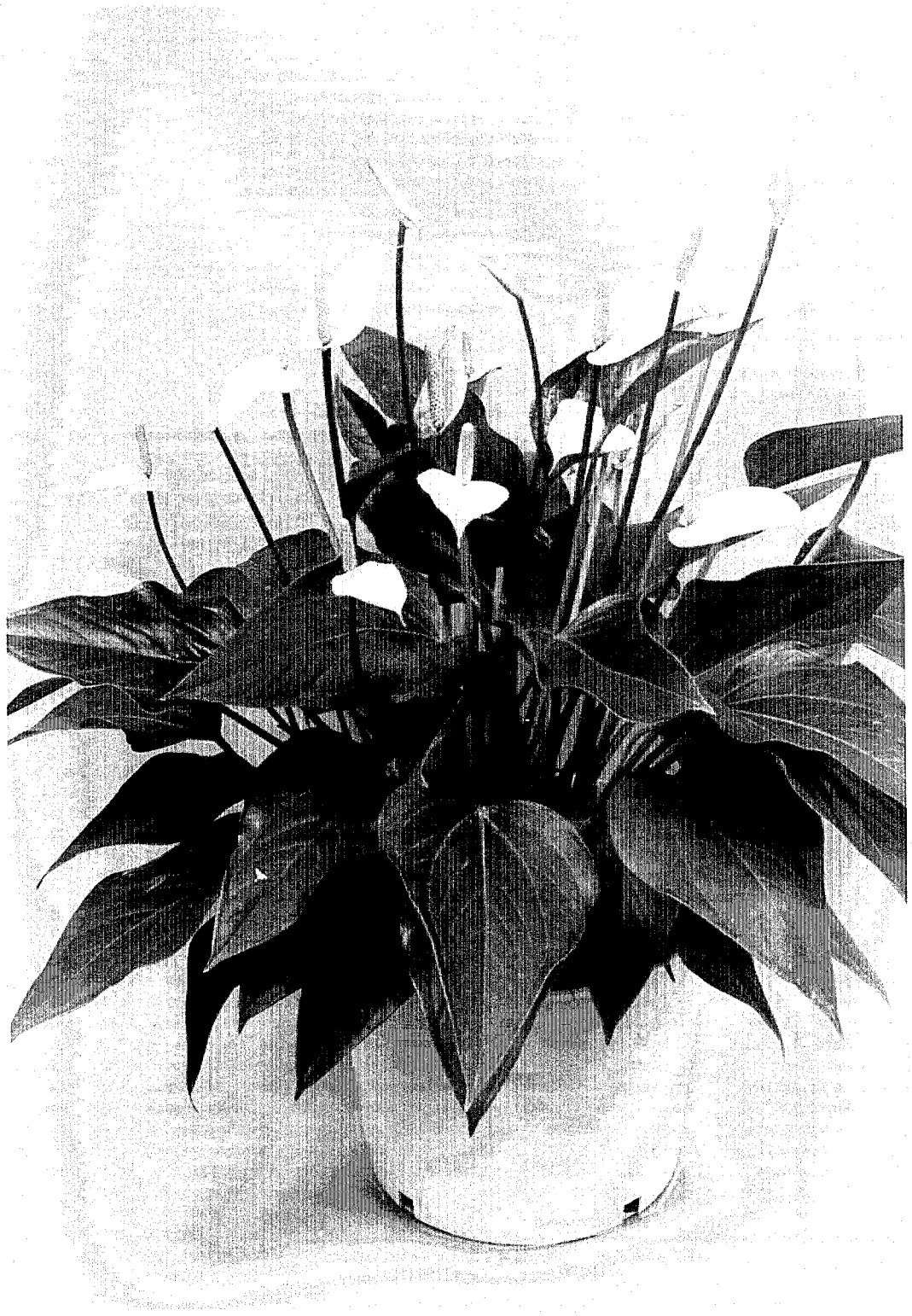

* * * * *